United States Patent [19]
Shanbrom

[11] Patent Number: 5,858,641
[45] Date of Patent: Jan. 12, 1999

[54] DISINFECTANT DYE REMOVAL FROM BLOOD AND BLOOD FRACTIONS USING A POROUS POLY(VINYL ALCOHOL-ACETAL) COPOLYMER

[75] Inventor: Edward Shanbrom, Santa Ana, Calif.

[73] Assignee: Shanbrom Technolgies, LLC, Ojai, Calif.

[21] Appl. No.: 718,642

[22] Filed: Sep. 17, 1996

[51] Int. Cl.$^6$ .................................................. A01N 1/02
[52] U.S. Cl. ................................ 435/2; 210/633; 210/660
[58] Field of Search .................. 435/2; 210/633, 210/660

[56] References Cited

U.S. PATENT DOCUMENTS

| | | |
|---|---|---|
| 4,305,390 | 12/1981 | Swartz . |
| 4,548,927 | 10/1985 | Eaton . |
| 5,639,376 | 6/1997 | Lee et al. .............................. 210/645 |

FOREIGN PATENT DOCUMENTS

| | | |
|---|---|---|
| 48-8574 | 3/1973 | Japan . |

OTHER PUBLICATIONS

"The Pharmacological Basis of Therapeutics—Germicides, Fungicides and Parasiticides", Goodman & Gilman—1941.

*Primary Examiner*—Sandra E. Saucier
*Attorney, Agent, or Firm*—Stefan J. Kirchanski; Graham & James LLP

[57] ABSTRACT

A process for removing disinfectant dye such as methylene blue from blood, a liquid blood fraction or other perishable liquid to which disinfectant dye has been added. The process employs a filter of polyvinyl alcohol-acetal copolymer. This material shows exceptional avidity for disinfectant dyes, readily removing them from blood or blood fractions while having little or no effect on subsequent chemicals analysis of the treated material. The filter material is a porous matrix that releases no particles or fines into the blood product, and its white color readily shows the capture of the blue dye. Disinfectant dyes are used to extend the shelf life of platelet concentrates with the dyes being removed by a PVAA filter prior to transfusion into a patient. Also, triglycerides may also be removed from plasma or other solutions by passage through a porous matrix of poly(vinyl alcohol-acetal) copolymer.

8 Claims, 1 Drawing Sheet

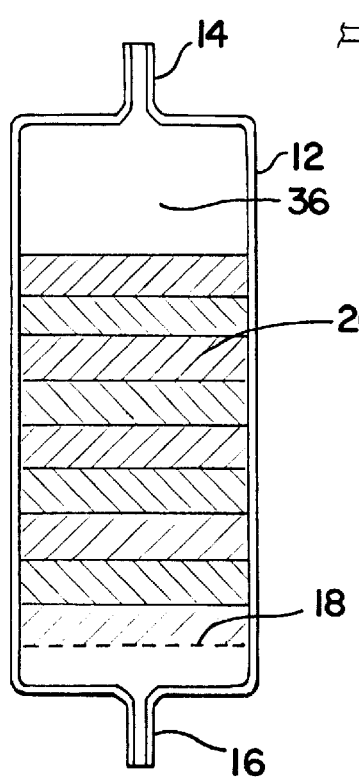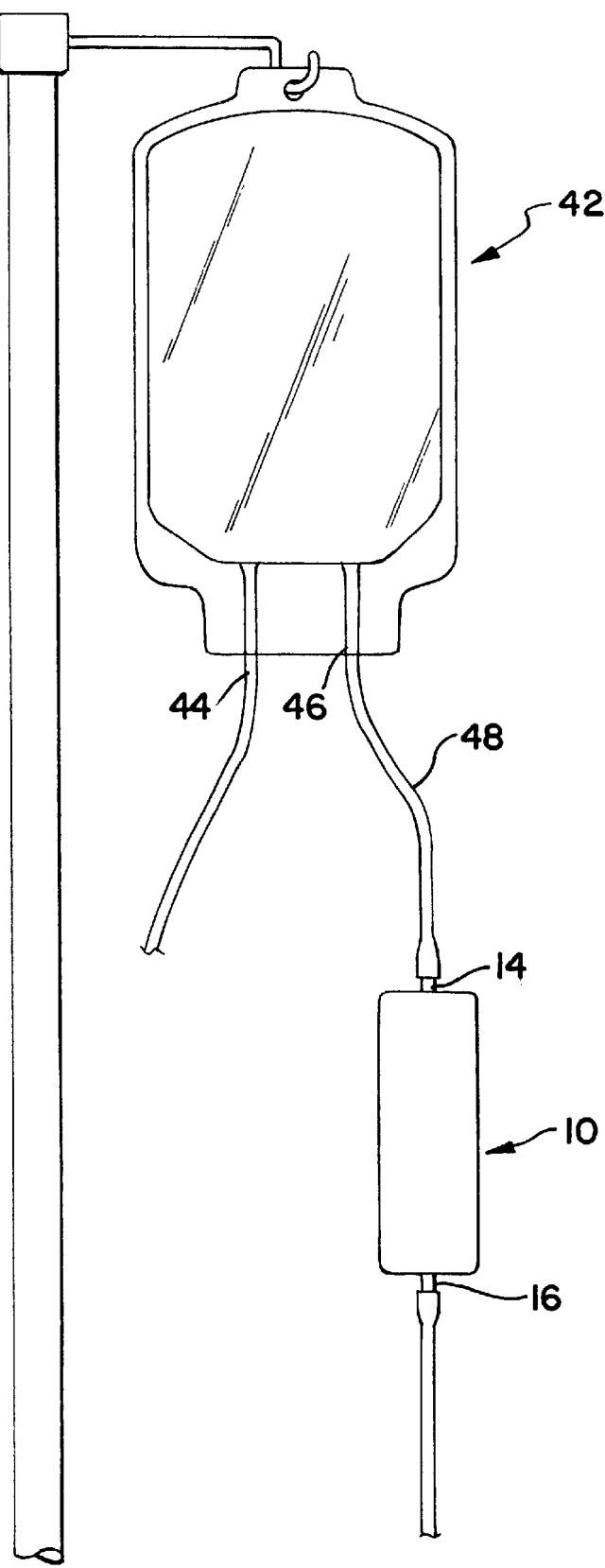

DISINFECTANT DYE REMOVAL FROM BLOOD AND BLOOD FRACTIONS USING A POROUS POLY(VINYL ALCOHOL-ACETAL) COPOLYMER

BACKGROUND OF THE INVENTION

1. Field of the Invention

The present invention is related to the medical field of hematology and, more particularly, for an improved method and device for the removal of disinfectant dyes such as methylene blue from blood, blood fractions or other perishable liquids to which the dyes have been added for disinfecting purposes.

2. Description of Related Art

At the present time one has only to mention human blood and blood transfusion to elicit anxiety related to fear of somehow contracting AIDS (Acquired Immunodeficiency Syndrome) from tainted blood. While it is true that various antibody-based and other tests have made it possible to remove the vast majority of HIV (Human Immunodeficiency Virus, the causative agent of AIDS) infected blood from our blood supply, the current status of AIDS as an incurable fatal disease makes even a relatively small risk unacceptable to many.

The risk of infection can be further reduced both by improving the sensitivity of diagnostic tests applied to the blood and by developing methods to disinfect the blood so that infected blood that evades the tests can be rendered substantially harmless. An additional advantage to the option of disinfecting blood is that there are many other blood-borne viral diseases besides AIDS. The public is generally aware of the several types of hepatitis that may be contracted from blood transfusions. These diseases range from being merely debilitating to being fatal as in the case of fulminating hepatitis or liver cancer, which is strongly correlated with certain forms of hepatitis. There are undoubtedly many other blood-borne viral pathogens that are as yet undiscovered.

One means of eliminating or removing viruses from blood is the use of "phototherapy" or "photodisinfection." Virtually all pathogenic agents, with the possible exception of "prions," are known to contain nucleic acids as their genetic material. Whereas nucleic acids in human cells are packaged by proteins and protected by the cytoplasm and the nuclear envelope, in typical viruses they are more exposed. This makes it possible to more readily cause photochemical damage to them. Nucleic acids naturally absorb light energy in the ultraviolet range. In fact, much of the skin damage caused by sunlight is due to photochemical damage to nucleic acids.

There have been some experiments with using ultraviolet light to disinfect blood, but this has generally not proven satisfactory. Levels of ultraviolet radiation that inactivate blood-borne pathogens are difficult to administer and may also cause damage to cellular and protein components of the blood. Furthermore, ultraviolet radiation can be difficult to work with and may damage or fail to penetrate materials commonly used in blood handling.

It is well-known that a chromophore absorbing light in the normal visible spectrum can be used to indirectly effect disinfection. Essentially, the chromophore absorbs visible light and becomes "excited." This extra energy from absorbing the light has to go somewhere: it can be converted into heat in the form of accelerated molecular vibration of the chromophore; it can be reemitted as fluorescence; or it can be used up in a photochemical reaction. Certain chromophores such as the thionine dye methylene blue (3,7-bis (dimethylamino)-phenazthionium chloride), when excited, is able to potentiate chemical reactions in nucleic acid. These photochemical reactions alter the structure of the nucleic acid and render it nonfunctional. Since living cells generally exclude the methylene blue, it is viral nucleic acids that are primarily liable to damage.

Although methylene blue is generally considered to be nontoxic, there is some trepidation at adding this material to blood and blood products for medical use. It is possible to remove methylene blue with binding substances such as activated charcoal. Unfortunately, many other substances stick to charcoal and are removed, thereby altering clinical chemistry and other diagnostic tests and potentially harming the quality of the transfused blood or blood product.

In addition, methylene blue and a number of other dyes are known to have "disinfectant" properties. This means that even in the absence of light these dyes may inhibit the growth of various microbes, especially bacteria. The cause of this disinfectant property is not entirely known. Since many of the disinfectant dyes have oxidation-reduction (redox) potentials in the range of many electron transport components of oxidative metabolism, it seems possible that these dyes operate by "short circuiting" these electron transport pathways. Generally the dyes show differential activity towards gram-negative versus gram-positive bacteria with electronegative dyes being more effective on gram-negative bacteria and electropositive dyes being more effective on gram-positive bacteria.

Human blood and blood fractions frequently have a limited shelf life because bacteria accidentally introduced into the blood from the skin of the blood donor multiply in the blood and eventually render it unusable. Until now no effective way of dealing with these bacterial contaminants has been developed. Addition of antibiotics or chemical disinfectants, while effective, is undesirable because of the problem of introducing these agents into the patient along with the blood or blood fraction.

OBJECTS AND SUMMARY OF THE INVENTION

Therefore, it is an object of the present invention to provide a means for readily removing disinfectant dyes from blood, blood products or other perishable liquids to which the dyes have been added to eliminate viral contamination or prevent bacterial reproduction;

It is also an object of the current invention to provide a material and method for removing disinfectant dyes without seriously altering the chemistry of the treated blood or blood product; and It is a further object of the current invention to provide a dye removal material that allows ready visual assessment of removed dye.

These and additional objects that will become apparent to one of ordinary skill in the art upon reading the following specification are provided through the use of a filter of polyvinyl alcohol-acetal copolymer. This material shows exceptional avidity for a number of disinfectant dyes, readily removing them from blood or blood fractions while having limited effects on subsequent chemical analysis of the treated blood. The filter material is generally a porous matrix that releases no particles or fines into the treated product, and its white color readily indicates the capture of the dye. Addition of disinfectant dyes, followed by later removal, provides a method for extending the useful life of purified platelet fractions.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings:

FIG. 1 shows a cross-sectional diagram of a simple filter device used in the present invention; and FIG. 2 shows an apparatus for utilizing the present invention to extend the shelf life of platelet concentrates.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a method of using polyvinyl alcohol-acetal copolymer to remove disinfectant dyes from blood and blood products.

By "disinfectant dyes" is meant any of a number of artificial organic dyes, generally known as "vital dyes," including methylene blue and related thionine dyes (electronegative), acridine orange, acridine yellow and related acriflavine (acridine) dyes (electropositive), quinacrine and its derivatives, brilliant green, gentian violet, crystal violet and related triphenyl methane dyes (electropositive), and bis naphthalene dyes such as trypan blue and trypan red.

The polyvinyl alcohol-acetal (PVAA) presently preferred for use in the present invention is a special medical grade of the polymer known as MEROCEL® manufactured by the Merocel Corporation of Mystic, Conn. This material is already widely used as surgical sponges and packings. It has a uniform pore size and releases neither fines nor solutes. While its avidity for disinfectant dyes is generally shared by PVAA from other sources, the desirable porosity properties and freedom from contaminating solutes are not known to be readily available in alternate PVAA materials. While PVAA is generally used in the form of sponge-like porous pads, it can also be used as a chopped or granulated material. An unusual property of PVAA is its apparent property to bind many electronegative as well as electropositive dyes. Most binding materials bind only negative or positive dyes and not both.

Virtually any filter holder or column chromatography device can be used to practice the present invention. FIG. 1 shows an example of a filter or column device 10 for use in the present invention. The filter device 10 has a cylindrical hollow body 12 made from polycarbonate plastic but acrylic, polysulfone, or any of a number of optically transparent materials, such as glass, can be employed. The filter device 10 has an upper inlet 14 and a lower outlet 16. These are advantageously equipped with luer fittings to accommodate components commonly used in blood-processing. However, luer-lock, swage-lock or any of a number of additional fitting types (i.e., pipe fittings) could be readily substituted. It will be readily appreciated that a key factor is that the filter material should be visible inside the device 10 so that the absorption of dye can be observed and a new device 10 can be placed into service when the original device becomes saturated with dye (as evidenced by the dye color approaching the lower outlet 16).

In actual use a filter chamber 36 generally contains one or more PVAA filter pads. To ensure complete removal of disinfectant dye it is advantageous to use a plurality of pads almost filling the filter chamber 36. As the pads absorb dye, they become increasingly colored (this presupposes that plasma or relatively colorless blood fractions are being processed; in the case of whole blood the filter must be rinsed to observe the color). In selecting the proper volume of PVAA (i.e., the number of filter pads) it is preferred to use a sufficient depth of PVAA that some totally white PVAA remains at the bottom of the filter compartment 36 at the end of filtration. This ensures that the final product will be free of disinfectant dye.

The PVAA filter pads are supported by a frit-disc 18 or some similar permeable structure. The frit-disc 18 is relatively thin and is composed of suitable plastic or other inert material, alternatively it can consist of a piece of stainless steel or other screening or a perforated metal disc. The disc 18 is perforated so that it can support the PVAA pad while not significantly impeding the flow of liquid. As an alternative to PVAA filter pads, it is also possible to fill the filter device 10 with granular or chopped PVAA material. A potential advantage of such material is that it can be readily poured into the filter device 10. When using granular or chopped material it is especially critical that the frit disc 18 or its equivalent be selected with a structure that resists clogging by the granular PVAA.

In normal use a source of plasma or blood is attached by means of tubing to the upper inlet 14. Often the source will be a blood 42 which is hung above the device 10 so that liquid will flow through the inlet 14 by gravity. Alternatively, a peristaltic pump can be used to push liquid through the inlet 14. It will be appreciated that a major goal of the invention is to allow the blood to be processed without danger of contamination of personnel or laboratory equipment. Therefore, it is preferable that all components be disposable so potentially infected blood is kept out of contact with personnel or permanent laboratory equipment.

After the complete batch of liquid requiring removal of dye has passed into the device 10 and out through the outlet 18 into a receiving vessel such as a fresh blood bag (not shown), there may be a considerable volume of liquid retained by the PVAA. In the case of purified blood factors, such as coagulation concentrates, this volume of retained liquid can have a considerable economic value. Therefore, after all the liquid had flowed in through the inlet 16, a vacuum may be pulled through the outlet port 18 or positive air pressure may be applied through the inlet 16 to extract this retained liquid. Alternatively, the PVAA pads can be mechanically squeezed to release the bound liquid.

EXAMPLE 1

To test the ability of the present invention to remove the disinfectant dye methylene blue from human blood, an experiment was carried out using methylene blue to treat either human plasma or an aqueous solution of human serum albumin (HSA). Albumin was used because it is a major component of blood plasma and is noted for its ability to bind many different substances with great affinity. Thus, it represents a worst case situation for the removal of methylene blue. On the other hand, human plasma, which comprises a mixture of many components, represents a good standard for judging whether the filtration process removes any other substances besides methylene blue. One milliliter of a 4.0 mg/ml stock solution of methylene blue in water (final methylene blue concentration of 0.08 mg/ml) was added to 50 ml of human plasma and to 50 ml of a 4% (weight by volume) aqueous solution of HAS. This represents a higher concentration of methylene blue than is commonly used in photodisinfection processes. The methylene blue stock solution was essentially opaque, and its addition at 0.08 mg/ml produced dark blue plasma or albumin solution.

In both cases the filter device 10 of FIG. 1 was filled with 25 CF 150 Merocel pads (26 mm diameter discs, Catalog #820170). After passing the HSA solution through, the top 12 pads were clearly colored blue with the top pad being very dark while the twelfth pad was practically colorless. The lower 13 pads remained colorless. Similar results were observed with the human plasma. In both cases the filtered solution was colorless indicting essentially complete removal of the methylene blue. Samples of the human plasma both before and after filtration through the PVAA were submitted for clinical chemistry analysis; the results are given in Table 1.

| Analyte | Control Plasma | Methylene Blue Treated Plasma |
|---|---|---|
| Amylase (U/L) | 64 | 67 |
| CPK (U/L) | 55 | 54 |
| LDH (U/L) | 111 | 120 |
| SGOT (U/L) | 17 | 16 |
| SGPT (U/L) | 13 | 13 |
| Lipase (U/L) | 0 | 0 |
| Total Protein (g/dl) | 5.9 | 6.5 |
| Albumin (g/dl) | 3.3 | 3.6 |
| Triglycerides (mg/dl) | 91 | 0 |
| Cholesterol (mg/dl) | 139 | 152 |
| Uric Acid (mg/dl) | 4.3 | 3.1 |
| BUN (mg/dl) | 13 | 12 |
| Creatinine (mg/dl) | 0.8 | 0.8 |
| Glucose (mg/dl) | 333 | 333 |
| Total bilirubin (mg/dl) | 0.2 | 0.3 |
| Indirect bilirubin (mg/dl) | 0.2 | 0.3 |
| Direct bilirubin | 0 | 0 |
| Sodium (mEq/L) | 166 | 166 |
| Potassium (mEq/L) | 3.4 | 3.4 |
| Chloride (mEq/L) | 80 | 80 |
| $CO_2$ (mEq/L) | 21 | 21 |
| Calcium (mg/dl) | 7.1 | 9 |
| Phosphorus (mg/dl) | 11.2 | 11.1 |

With the exception of triglycerides the results were not statistically different indicating that while the PVAA is an excellent binder of methylene blue, it has little or no affinity for other medically important components of plasma. The results with triglycerides are extremely interesting and potentially useful. Apparently methylene blue dye is sufficiently lipophyllic to preferentially partition into the triglycerides. When the methylene blue binds to the PVAA it also binds the triglycerides to the PVAA. In this example a given weight of methylene blue is able to bind at least ten times its weight in triglycerides (i.e., 0.08 mg/ml methylene blue removes 0.91 mg/ml triglycerides). This provides a unique method for removing triglycerides, for example, in preparing a clinical chemistry control material. It is also conceivable that this method could be used to remove triglycerides directly from the blood of hyperlipemic patients using a "plasmapheresis" type setup. That is, a system that would withdraw blood from the patient, add methylene blue, filter the methylene blue-blood through PVAA to remove the methylene blue and triglycerides and then return the blood to the patient.

Because albumin generally binds methylene blue with considerable affinity, the PVAA binding of methylene blue also offers a convenient means of purifying albumin. If PVAA is saturated with methylene blue, say by treating it with a 1% weight/volume aqueous methylene blue solution followed by extensive washing to remove loosely bound dye, the resulting blue PVAA can be used as an albumin purifying reagent or to remove albumin from samples prior to diagnostic tests that might be negatively impacted by albumin.. When albumin-containing solutions are passed through the blue PVAA, a large amount of albumin becomes bound to the PVAA. The bound albumin can be released by changing the pH or applying other mild denaturing conditions well known to those of ordinary skill in the art. It should also be apparent that albumin capture is also amenable to a "plasmapheresis" set up whereby albumin can be selectively harvested from donors without actually permanently removing significant volumes of whole blood.

EXAMPLE 2

Tests were made to determine the ability of methylene blue to inhibit *Yersinia enterocolitica, Serratia marcesceus* and *Staphylococcus aureus,* common skin surface bacteria that often contaminate blood used for transfusion purposes. Aliquots of human plasma were spiked with bacteria (one species of bacteria for each aliquot) at a concentration of 100 organisms per milliliter. Then the aliquots were divided into five parts: one part served as a control, a second part was brought to 100 $\mu$M methylene blue, a third part was brought to 50 $\mu$M methylene blue, a fourth part was brought to 10 $\mu$M methylene blue, and a fifth part was brought to 5 $\mu$M methylene blue. The aliquots were incubated overnight at room temperature, filtered through a sufficient depth of PVAA to remove all visible traces of methylene blue, and one milliliter of each treatment was deposited on the surface of a nutrient agar Petri plate. The plates were rocked to spread the sample over the agar surface and were then incubated at 37° C. for 24 hours. The bacterial colonies were then counted; the results shown in Table 2.

TABLE 2

| | Y. enterocolitica | S. marcescens | S. epidermidis |
|---|---|---|---|
| 100 $\mu$M | 0 colonies | 0 colonies | 7 colonies |
| 50 $\mu$M | 0 colonies | 0 colonies | 18 colonies |
| 10 $\mu$M | 0 colonies | 0 colonies | 53 colonies |
| 5 $\mu$M | 0 colonies | 0 colonies | 78 colonies |
| 0 $\mu$M (control) | 98 colonies | 106 colonies | 101 colonies |

These results indicate that the methylene blue treatment was outstandingly effective at killing *Y enterocolitica* and *S. marcescens,* gram-negative bacteria, even at very low concentrations. The dye, however, was less effective at eliminating *S. epidermidis,* a gram-positive bacterium, except at relatively high concentrations. It is a common observation that agents that effect gram-negative bacteria are often ineffective on gram-positive species. However, since the present invention allows for effective removal of even high concentrations of dye, it may be feasible to effectively inhibit even *S. epidermidis.*

EXAMPLE 3

The ability of PVAA to bind acridine orange was tested using a 4.0 mg/ml solution of the dye in distilled water. One milliliter of this stock solution was added to 50 ml each of distilled water, human plasma, and 4% HAS. Each of these solutions was then filtered through a stack of 25 CF150 Merocel pads. Complete removal of the dye was achieved in each case indicating that PVAA's affinity for acridine orange is quite high. This makes it possible to employ acridine orange addition to blood or blood products as a means to destroy protozoan pathogens such as plasmodia (malaria) or trypanosomes (sleeping sickness). Acriflavines and related dyes are very effective at killing these organisms, but are far too toxic to use in blood or blood products. The present invention makes it possible to effectively treat blood or blood products to destroy these parasites (some of which may actually be within the red blood cells) and to then remove the dye before administering the blood or blood products to patients.

EXAMPLE 4

Worry about bacterial contamination has caused the authorities to reduce the permissible shelf life of platelet concentrates from seven days to five days or less. The use of platelet concentrates is vital in the management of a number of important disease states, and the currently inadequate supply of platelet concentrates could be extended by returning the platelet concentrate dating to seven days or longer. To this end platelet concentrates were spiked with bacterial contaminants and methylene blue added to see if disinfectant dye can be used to extend platelet concentrate life.

Platelet concentrates were spiked with 100 organisms per milliliter of *S. marcescens, Y. enterocolitica* or *S. epidermidis*. Methylene blue was added at 100 $\mu$M, 50 $\mu$M, 10 $\mu$M or 5 $\mu$M and the samples were incubated at room temperature for 96 hours. After this incubation the samples were plated onto nutrient agar and incubated at 37° C. for 24 hours. Table 3 shows the results of colony counts of the agar plates.

TABLE 3

| Methylene Blue | S. marcescens | Y. enterocolitica | S. epidermidis |
| --- | --- | --- | --- |
| 100 $\mu$M | 0 colonies | 0 colonies | 12 colonies |
| 50 $\mu$M | 0 colonies | 0 colonies | 24 colonies |
| 10 $\mu$M | 0 colonies | 0 colonies | 76 colonies |
| 5 $\mu$M | 0 colonies | 0 colonies | 91 colonies |
| 0 $\mu$M (control) | 70 colonies | 50 colonies | 100 colonies |

These results indicate that methylene blue in the presence of platelets is still very effective at inhibiting gram-negative bacteria even at low methylene blue concentrations. More importantly, platelet morphology and function did not appear to be affected by methylene blue as determined by standard tests. Furthermore, removal of methylene blue by passing the platelet concentrates through PVAA filters did not negatively impact platelet function or morphology. Therefore, it appears that adding methylene blue to platelet concentrates on a regular basis can be used to significantly retard bacterial growth and, thereby, extend the shelf life of the platelet concentrate.

While it is possible to add the methylene blue at various points during the processing of the concentrate, it is preferred to provide platelet bags already containing the required amount of dye as a dry powder. When platelet containing solutions are dispensed into the bag, the dye will dissolve and immediately begin to destroy bacteria. Immediately before actual use of the platelet concentrate the solution can be run through a PVAA-containing filter device 10 similar to the one in FIG. 1. FIG. 2 shows a blood bag 42 which already contains the proper amount of methylene blue. When a platelet-containing solution is added to the bag through an inlet 44, the methylene blue is dissolved and immediately begins to protect against bacterial growth. When the platelets are to be given to a patient, the solution exits the bag 42 through an outlet 46 is passed through one of the PVAA filter devices 10 to remove the methylene blue. The blood bag 42 and the filter 10 can advantageously be configured as a kit as shown in FIG. 2 with tubing 48 provided to conduct the solution from the blood bag 42 to the filter 10 and thence to the patient.

EXAMPLE 5

In view of the known tendency for acidic disinfectant dyes to be effective against different organisms than basic disinfectant dyes there may be a benefit to using mixtures of both dye types. However, it was not apparent whether the two oppositely charged dyes can be simultaneously removed by a PVAA filter. Also, the older literature teaches that the acidic dyes are most effective at acid pH's while the basic dyes are more effective at alkaline pH's. An experiment was carried out where methylene blue was added to a test solution to a concentration of 50 $\mu$M. Then crystal violet was added to bring the solution to 0.025% crystal violet. When 50 ml of this solution was rapidly filtered through 25 pads PVAA (CF 150 Merocel pads), all visible traces of both dyes were removed. To test the disinfectant ability of these dyes various dye combinations were mixed with plasma and spiked with *Pseudomonas aeruginosa* (the most resistant gram negative bacteria) and/or *Staphylococcus epidermidis* (the most resistant gram positive bacterium) at 100 organisms per milliliter. The tests were carried out as described above under Example 2. In plasma there was a complete kill of *S. epidermidis* by crystal violet and a complete kill of *S. epidermidis* and *P. aeruginosa* by a mixture of the two dyes. Furthermore, when packed red blood cells were spiked with *S. epidermidis*, the crystal violet still effected a complete kill.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A process for removing methylene blue from blood or a fraction derived from blood to which methylene blue has been previously added, comprising passing the blood or blood fraction through a thickness of porous of polyvinyl alcohol-acetal copolymer sufficient to bind essentially all of the methylene blue while allowing a majority of the blood or blood fraction to pass through.

2. A process for removing methylene blue from blood or a fraction derived from blood to which methylene blue has been previously added, the process comprising the steps of:
    passing the blood or blood fraction through a bed of porous polyvinyl alcohol-acetal copolymer of sufficient thickness to bind essentially all of the methylene blue while allowing a majority of the blood or blood fraction to pass; and
    after the blood or blood fraction is finished flowing through the bed, expressing retained blood or blood fraction.

3. A process for extending shelf life of platelet concentrates comprising the steps of:
    adding methylene blue to platelet concentrate;
    storing the platelet concentrate until the concentrate is needed; and passing the concentrate through a thickness of porous polyvinyl alcohol-acetal copolymer of sufficient thickness to bind essentially all the methylene blue prior to administering the platelet concentrate to a patient.

4. The process of claim 3, wherein the methylene blue is added to a concentration of between 1 $\mu$M and 100 $\mu$M.

5. A process for removing triglycerides from an aqueous solution comprising the steps of:

adding methylene blue to the solution; and passing the solution through a thickness of porous polyvinyl alcohol-acetal copolymer of sufficient thickness to bind essentially all the methylene blue, whereby triglycerides are removed along with the methylene blue.

6. The process of claim 5, wherein weight of methylene blue added is selected to be at least about one tenth of weight of the triglycerides to be removed.

7. A process for removing disinfectant dye from blood or a fraction derived from blood to which the disinfectant dye has been previously added, comprising passing blood or blood fraction through a thickness of porous polyvinyl alcohol-acetal copolymer sufficient to bind essentially all of the disinfectant dye while allowing a majority of blood or blood fraction pass through.

8. The process of claim 7, wherein the disinfectant dye is selected from the group consisting of methylene blue, acridine orange, gentian violet, brilliant green, acridine yellow, quinacrine, trypan blue, and trypan red.

* * * * *